US010828396B2

United States Patent
Li et al.

(10) Patent No.: US 10,828,396 B2
(45) Date of Patent: Nov. 10, 2020

(54) DEGRADABLE MAGNESIUM-CONTAINING CALCIUM PHOSPHATE-CALCIUM SULFATE POROUS COMPOSITE BIOLOGICAL SCAFFOLD

(71) Applicant: Yaping Li, Ningbo (CN)

(72) Inventors: Yaping Li, Ningbo (CN); Sang Li, Ningbo (CN); Haijiao Mao, Ningbo (CN); Tingting Tang, Ningbo (CN); Jun Fu, Ningbo (CN); Hanfeng Xiong, Ningbo (CN); Lei Nie, Ningbo (CN); Jianmin Zheng, Ningbo (CN); Guofeng Zhang, Ningbo (CN)

(73) Assignee: Yaping Li, Ningbo (CN)

( * ) Notice: Subject to any disclaimer, the term of this patent is extended or adjusted under 35 U.S.C. 154(b) by 0 days.

(21) Appl. No.: 16/311,688

(22) PCT Filed: Jan. 4, 2017

(86) PCT No.: PCT/CN2017/000100
§ 371 (c)(1),
(2) Date: Dec. 20, 2018

(87) PCT Pub. No.: WO2017/219654
PCT Pub. Date: Dec. 28, 2017

(65) Prior Publication Data
US 2019/0224371 A1    Jul. 25, 2019

(30) Foreign Application Priority Data

Jun. 20, 2016  (CN) .......................... 2016 1 0446808

(51) Int. Cl.
| | |
|---|---|
| *A61L 27/40* | (2006.01) |
| *A61L 27/46* | (2006.01) |
| *A61L 27/58* | (2006.01) |
| *A61L 27/36* | (2006.01) |
| *A61L 27/56* | (2006.01) |

(52) U.S. Cl.
CPC ............. *A61L 27/40* (2013.01); *A61L 27/365* (2013.01); *A61L 27/3608* (2013.01); *A61L 27/3687* (2013.01); *A61L 27/3691* (2013.01); *A61L 27/46* (2013.01); *A61L 27/56* (2013.01); *A61L 27/58* (2013.01); *A61L 2430/02* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 2005/0184418 A1 | 8/2005 | Lin et al. | |
| 2013/0224261 A1* | 8/2013 | Shen | A61K 9/5115 424/400 |

FOREIGN PATENT DOCUMENTS

| | | | | |
|---|---|---|---|---|
| CN | 1207060 C | * | 6/2005 | |
| CN | 102106765 A | | 6/2011 | |
| CN | 101671848 B | * | 10/2011 | |
| CN | 102268722 B | * | 6/2013 | |
| CN | 103520779 A | * | 1/2014 | |
| CN | 105107023 A | * | 12/2015 | ......... A61L 27/3608 |
| CN | 105169482 A | | 12/2015 | |
| CN | 105582574 A | * | 5/2016 | ............. A61L 27/36 |
| CN | 105582574 A | | 5/2016 | |
| CN | 105597158 A | * | 5/2016 | ............. A61L 27/36 |
| CN | 105597158 A | | 5/2016 | |
| WO | 2012101428 A1 | | 8/2012 | |

OTHER PUBLICATIONS

Marchi, Materials Research Bulletin, 42, 2007 (Year: 2007).*
Podaropoulos, Oral Implantology, 35, 1, 2009 (Year: 2009).*
Johan Van Der Stok et al. "Bone substitutes in the Netherlands—a systematic literature review", Acta Biomater. Feb. 2011;7(2):739-50.

* cited by examiner

*Primary Examiner* — Susan T Tran
*Assistant Examiner* — William Craigo
(74) *Attorney, Agent, or Firm* — Bayramoglu Law Offices LLC

(57) ABSTRACT

A method for preparing a degradable magnesium-containing calcium phosphate-calcium sulfate porous composite biological scaffold by subjecting a calcined bovine cancellous bone mineral porous scaffold to a treatment using a ternary system containing a magnesium source, a sulfur source and a phosphorus source, taking out and drying, and subjecting to a high-temperature calcination. The degradable magnesium-containing calcium phosphate-calcium sulfate porous composite biological scaffold has good three-dimensional interconnected mesh structure, osteoconductivity, degradability, good mechanical strength and biocompatibility, simultaneously. At the same time, calcium sulfate whiskers with larger length-diameter ratio grow in the mesh, thereby increasing the specific surface area of the material and possibly improve the adhesion of cells. The composite biological scaffold may have potential osteoinductivity due to the effective addition of the osteogenic active ionized magnesium and the calcium sulfate which can produce a local high-calcium environment when degraded.

16 Claims, 3 Drawing Sheets

DEGRADABLE MAGNESIUM-CONTAINING CALCIUM PHOSPHATE-CALCIUM SULFATE POROUS COMPOSITE BIOLOGICAL SCAFFOLD

CROSS REFERENCE TO RELATED APPLICATIONS

This application is the national phase entry of International Application No. PCT/CN2017/000100, filed on Jan. 4, 2017, which is based upon and claims priority to Chinese Patent Application No. 201610446808.1, filed on Jun. 20, 2016, the entire contents of which are incorporated herein by reference.

TECHNICAL FIELD

The present invention relates to the field of medical materials, and particularly to a degradable magnesium-containing calcium phosphate-calcium sulfate porous composite biological scaffold.

BACKGROUND

Bone grafting is required for treating bone defects caused by accidents, bone diseases, war injuries or orthopedic surgeries. Bone grafting is a kind of tissue transplantation with a number of cases only less than that of blood transfusions. More than 1 million patients need bone grafting each year in the United States. According to the population proportion, it is inferred that more than 4 million patients need bone grafting in China and more than 20 million patients need bone grafting worldwide every year. Currently, autologous bone grafting is the "golden standard" for the treatment of bone defects, but it brings new trauma to patients, and causes certain complications in the bone graft harvest site. Moreover, the sources of autologous bone are limited, and the autologous bone grafting is not suitable for some patients such as children and the elderly. Research and development of bone substitute materials is one of the focuses of current medical research. Research on the mechanism of interaction between bone substitute materials and the body is included in the 12$^{th}$ Five-Year National Plan.

The bone minerals constituting human bone include elements such as Ca, P, C, O, H, S, Fe, Mg, Cu, Si, Zn, Mn, Na, K, etc. In the mineralization process of human bone, there are extensive homogenous substitute behaviors, and human bone has complex compositions and structures. In the design process of bone tissue engineering scaffold or artificial bone, the complex compositions and structures of human bone, a severely mineralized tissue, are the most important issues to be considered. The function of human bone cannot be completely replaced by the limited properties provided by a single material. More importantly, scaffolds must further provide a three-dimensional porous microstructure for the regeneration of bone tissue to guide the differentiation and proliferation of the cells, and should be capable of maintaining or quickly obtaining sufficient mechanical strength to achieve the mechanical requirements of the material being replaced. The ideal bone graft substitute materials or the bone tissue engineering scaffold materials should meet the following conditions: 1) good osteoconductivity, three-dimensional interconnected mesh structure with ideal aperture, and highest possible porosity and specific surface area; 2) bone inductivity property; 3) good biocompatibility, and surface chemical property and microstructure supporting the growth and functional differentiation of bone cells; 4) good biodegradability; 5) the portion of the material exerting osteoconduction function must have sufficient mechanical strength and supporting capacity; 6) easy to process; etc.

In a review in 2010, Johan et al. classified bone graft substitute materials available for clinical use in the Netherlands into four categories: 1. single-phase calcium-phosphorus materials include three kinds of hydroxyapatite transformed bioceramics, one kind of synthetic hydroxyapatite cement, and two kinds of β-tricalcium phosphate artificial ceramics; 2. composite materials include five kinds of synthetic cements having the following formulas: tetracalcium phosphate/dicalcium phosphate, 62.5% α-tricalcium phosphate/26.8% dicalcium phosphate anhydrous/8.9% calcium carbonate/1.8% hydroxyapatite, 73% β-tricalcium phosphate/21% monocalcium phosphate monohydrate/5% magnesium hydrogen phosphate trihydrate, tetracalcium phosphate/dicalcium phosphate/trisodium citrate, and α-tricalcium phosphate/calcium carbonate/monocalcium phosphate monohydrate, and two kinds of artificial ceramic having the following formulas: 80% tricalcium phosphate/20% hydroxyapatite, and 60% hydroxyapatite/40% β-tricalcium phosphate; 3. four kinds of paste or pellets prepared from single-phase calcium sulphate; and 4. one kind of silicon-containing bioactive glass. Currently, apatite and calcium sulphate are the most common bone graft substitute materials or components for bone graft substitute materials in clinical practice. At present, there is a lack of ideal bone graft substitute materials in clinical practice, which is mainly reflected in that the bone graft substitute materials available now cannot simultaneously possess properties such as the ideal three-dimensional interconnected mesh structure, maximum porosity and specific surface area, degradability, osteoconductivity, osteoinductivity, and mechanical strength, etc.

The artificial bones with a relatively ideal three-dimensional interconnected mesh microstructure that have been applied clinically are all transformed from animal materials. Two of the artificial bones are porous hydroxyapatite ceramic bones prepared by high temperature sintering and derived from bovine cancellous bone, characteristics thereof are that the three-dimensional interconnected mesh microstructure of natural bone minerals of bovine cancellous bone is retained, and the components are similar to the bone mineral components of human bone, having good biocompatibility, excellent osteoconductivity and perfect compressive strength; immune rejection of xenogeneic bone and the possibility of pathogen introduction can be avoided due to high temperature sintering procedures; and the processing is easy. Porous hydroxyapatite derived from bovine bone has a good porosity of 60%-90%, and the bovine bone resources are abundant. The aperture of the porous hydroxyapatite is 390-1360 µm, which is slightly larger than the ideal aperture, i.e., 150-400 µm, of bone graft substitute material and bone tissue engineering scaffold. Porous hydroxyapatite derived from bovine bone has good compressive strength of 1-20 MPa. The implantation of the porous hydroxyapatite derived from bovine bone in the body is beneficial to the recruitment of bone repair cells, the entry of blood vessels, and the exchange of oxygen and tissue fluid, providing good physiological activity space and adhesion support for bone repair cells. However, the great disadvantages are that the bone mineral "hydroxyapatite" obtained by performing high temperature sintering on the bovine cancellous bone is too stable, so that the degradation of the hydroxyapatite in the body is too slow, the solubility of the hydroxyapatite is lowest among the calcium-phosphorus bone graft substitute materials, and the degradation rate is far from matching the formation speed of a new bone; the hydroxyapatite cannot continuously release relatively high-concentration of osteogenic beneficial ions, such as calcium ions etc., lacking good osteogenic activity, which is not conducive to the repair and reconstruction of the bone.

The ideal degradation rate is another important requirement for artificial bone or bone tissue engineering scaffolds. The ideal degradation rate of artificial bone should match the formation speed of the new bones, and the artificial bone is gradually degraded while guiding the formation of new bone, thereby further providing space for the substitution by the new bone. Osteogenic beneficial ions such as calcium ions, which are continuously released during the degradation process of the artificial bone, provide mineral recombination components for the redeposition, reconstruction and metabolism of bone minerals. The degradation process may stimulate the formation of new bone, namely, the artificial bone possesses some degree of potential osteoinductivity. The excessive high degradation rate of artificial bone or bone tissue engineering materials is not conducive to providing sufficient space-time support and guidance for the bone repair process, while the excessive slow degradation rate will hinder the formation, substitution and shaping of new bone. The degradation of inorganic bone graft materials in vivo is mainly realized through two pathways: body fluid-mediated dissolution and degradation, and cell-mediated degradation. The dissolution and degradation process is a physical dissolution and degradation process, during which under the action of body fluids, materials and binders are hydrolyzed, and materials are gradually dissociated into granules, molecules and ions. While the cell-mediated degradation process is a biodegradation process which is mainly achieved by phagocytosis of macrophage and osteoclast to materials. The degradation process of inorganic bone grafting materials in vitro is related to its composition. The degradation rate of inorganic bone grafting materials is closely related to the granule size, porosity, specific surface area, crystallinity and solubility of the materials, among which solubility is the most important factor. In clinical practice, calcium sulfate has the highest degradation rate among the most common bone graft substitute materials (The time for complete degradation of calcium sulfate in vivo is 45-72 days, more than twice as fast as autologous bone). Hydroxyapatite has the slowest degradation rate among calcium-phosphorus materials (Non-porous massive hydroxyapatite cannot be completely degraded in vivo even for 10 years), but the degradation rate of the hydroxyapatite is much higher than the formation rate of new bone. Other calcium-phosphorous components such as tricalcium phosphate, calcium hydrophosphate, calcium dihydrogen phosphate, poly (calcium hydrogen phosphate), calcium pyrophosphate, etc., have a degradation rate between that of the calcium sulfate and that of the hydroxyapatite, thus having a relatively moderate degradation rate. In order to overcome the obvious disadvantages of calcined bovine cancellous bone porous hydroxyapatite, scientific and technical researchers have attempted to convert calcined bovine cancellous bone porous hydroxyapatite into tricalcium phosphate or complex phase apatite ceramics containing tricalcium phosphate in the past 20 years. Commonly known as Paris cement, elemental calcium sulphate paste and cement granules are the oldest materials used for bone defect filling and are even still in use. The reasons are that the Paris cement has the following characteristics. 1. good biotolerance; 2 good space filling characteristics; 3 relatively high absorption speed and complete biological absorptivity; 4, potential osteogenic activity; 5 good osteoconduction and is capable of providing space for bone repair due to relatively fast absorption. 0.2 g of calcium sulfate can be dissolved at room temperature in 100 ml of water. When calcium sulfate is degraded in vivo, a high-calcium environment is formed locally, which provides a calcium source for the formation of bone mineral in new bone tissue and promotes the mineralization of new bone by combining the calcium source with phosphate radicals in body fluids. The potential osteoinductive activity of calcium sulfate is related to the local high-calcium and acidic microenvironment in the dissolution process of calcium sulfate. The locally high-calcium environment formed by the degradation of calcium sulfate in vivo not only provides the calcium source for the formation of new bone, but also promotes the formation and differentiation of osteoblasts to varying degrees. The locally acidic microenvironment formed by the degradation of calcium sulfate in vivo may promote the micro-dissolution and degradation of human bone minerals, resulting in the exposure of osteogenic active protein, which is conducive to the formation of new bone. However, the calcium sulfate paste or granules currently used in clinical practice also have the common disadvantages of synthetic materials, that is, it is difficult to have an ideal three-dimensional interconnected mesh structure. At the same time, the time of the complete degradation of the calcium sulfate in vivo is 45-72 days, more than twice as fast as autologous bone. Therefore, it is difficult for the calcium sulfate to maintain continuous and stable osteoconduction support for the formation of new bone, and calcium sulfate cannot provide three-dimensional porous microstructure for the regeneration of bone tissue, that is, it lacks a structural basis with good osteoconductivity to introduce the repair cells and blood vessels into the implant, which is not conducive for the formation of new bone. Even if the calcium sulfate simple substance scaffold having a high porosity, a high specific surface area and a three-dimensional interconnected mesh structure is successfully prepared, the degradation rate is faster and the strength is worse. After the dissolution and degradation of the calcium sulfate material, the local microenvironment may be acidic, which may cause an inflammatory reaction. The advantages of synthetic composite materials are that by selecting the components with different degradation characteristics and adjusting the composition ratio of the components thereof, the degradation rate, pH value and other physical properties of the composite materials reach a particular balance, and more in-vivo active proteins (signal proteins) may be adsorbed to improve the biological activity of materials, thereby meeting the ideal requirements for bone graft substitute materials as much as possible.

In addition, the biological activity of calcium phosphate and other bio-based materials may be enhanced by the addition of bioactive ions. Previous studies have shown that these bioactive ions can effectively stimulate protein activity and promote cell growth and bone growth. The human body contains about 25 g of magnesium, which plays an important role in the process of bone formation and growth, and the aspects of maintaining the structure and function of bone cells, the metabolism and reconstruction of bone. Magnesium phosphate and calcium-based bone cement with low magnesium content can significantly improve the adhesion ability of cells. Magnesium-doped calcium phosphate bone cement has become an increasingly important novel biomaterial of bone repair because it can promote the formation of interface between implant materials and bone tissue. Magnesium-doped calcium phosphate bone cement is easy to prepare; and bone cements with a formula of 73% β-tricalcium phosphate/21% monocalcium phosphate monohydrate/5% magnesium hydrogen phosphate trihydrate have been clinically applied in western countries such as Netherlands. The magnesium-containing bone cement with a composite formula has degradability, can release osteogenic beneficial elements, such as calcium, phosphorus, magnesium, etc., and can be degraded and ion exchanged in vivo after transplantation, but does not have a three-dimensional interconnected mesh structure, which hinders the repair cells and blood vessels early into the interior of the implant, and therefore lacks a three-dimensional interconnected mesh structure basis with good osteoconductivity.

In the Applicant's previous work, the calcined bovine porous hydroxyapatite was successfully converted into apatite-calcium sulfate composite scaffold (Application No. 2016100250985), the calcined bovine porous hydroxyapatite was converted into degradable magnesium-containing composite apatite porous ceramic (Application No. 201610024391X), and the degradation characteristics of the calcined bovine porous hydroxyapatite are successfully improved while maintaining the ideal three-dimensional interconnected mesh structure and good mechanical strength. In the application No. 201610024391X, magnesium ions were also successfully doped into the crystal lattice of soluble calcium phosphate, forming magnesium-doped calcium phosphate with good degradation characteristics, such as magnesium-doped tricalcium phosphate, etc., and the material successfully releases active ionized magnesium and beneficial ionized calcium, etc. when dissolved and degraded. Applicant is now attempting to further integrate their advantages to transform calcined bovine porous hydroxyapatite into a magnesium-containing calcium phosphate-calcium sulfate composite porous biological scaffold having excellent degradability.

SUMMARY

The objectives of the present invention are to solve the problems that the bone graft substitute materials available now cannot simultaneously possess properties such as a good three-dimensional interconnected mesh structure, mechanical strength, degradability and biological activity, etc.; and transform the calcined bovine cancellous simple substance hydroxyapatite having a complex and exquisite three-dimensional interconnected mesh structure of natural bone minerals (calcined bovine cancellous bone mineral porous scaffold) into a degradable bone-active ionized magnesium-doped calcium phosphate-calcium sulfate composite scaffold material retaining the complex and exquisite three-dimensional interconnected mesh structure. The degradable magnesium-containing calcium phosphate-calcium sulfate porous composite biological scaffold of the present invention has good three-dimensional interconnected mesh structure, osteoconductivity, degradability, good mechanical strength and biocompatibility, simultaneously. At the same time, whisker growth of the calcium sulfate with larger length-diameter ratio in the mesh can increase the specific surface area of the material and possibly improve the adhesion of cells. The composite biological scaffold may have potential osteoinductivity due to the effective addition of the osteogenic active ionized magnesium and the calcium sulfate which can produce a local high-calcium environment when degraded. The composite biological scaffold may more closely satisfy the ideal conditions for bone graft substitute materials or bone tissue engineering scaffold materials.

The technical solutions adopted by the present invention to solve the technical problems thereof are as follows.

A degradable magnesium-containing calcium phosphate-calcium sulfate porous composite biological scaffold is obtained by subjecting a calcined bovine cancellous bone mineral porous scaffold to a treatment of a ternary system containing a magnesium source, a sulfur source and a phosphorus source, taking out and drying, and calcining at high temperature.

X-ray powder diffraction analysis shows that the composite biological scaffold materials are active ionized magnesium-containing calcium phosphate-calcium sulfate porous composite biological scaffold materials, such as calcium sulfate/magnesium-containing calcium phosphate/hydroxyapatite, calcium sulfate/poly (magnesium-containing calcium hydrogen phosphate)/hydroxyapatite, calcium sulfate/magnesium-containing calcium phosphate, calcium sulfate/magnesium-containing calcium phosphate/hydroxyapatite/calcium pyrophosphate, calcium sulfate/magnesium-containing calcium phosphate/calcium pyrophosphate, etc. The composite biological scaffold material contains magnesium-containing calcium phosphate components with a good degradation rate, such as magnesium-containing tricalcium phosphate or poly (magnesium-containing calcium hydrogen phosphate), calcium sulfate having relatively high absorption rate, complete biological absorptivity, and potential osteogenic activity. Some materials also contain hydroxyapatite and/or calcium pyrophosphate. The hydroxyapatite is the substance with the lowest dissolution and degradation rate among the calcium-phosphorus compounds; and the degradation rate of the calcium pyrophosphate may be closer to the formation rate of bone. Since the dissolution and degradation rates of the various components of the composite biological scaffold materials are different, the composite materials can achieve gradient degradation: the calcium sulfate is more rapidly dissolved and degraded, the content of magnesium-containing calcium phosphate is gradually reduced, and the mass proportion of hydroxyapatite is gradually increased. Since the composition and mass ratio of the composite biological scaffold materials are changed flexibly and effectively by changing the mass ratio, concentrations, time of impregnation and hydrothermal reaction, calcining temperature and time, etc., of the reactants in the compound formula, the degradation rate of the composite biological scaffold materials can be effectively regulated. For example, under the experimental conditions, with the increase of the amount of sulfur, the content of calcium sulfate may be gradually increased without changing other conditions; with the increase of the amount of phosphorus, the hydroxyapatite with a calcium to phosphorus ratio of 1.67 is gradually converted into a magnesium-containing tricalcium phosphate with a (calcium and magnesium) to phosphorus ratio of approximately 1.5, and a calcium pyrophosphate with a calcium to phosphorus ratio of 1. In a simulated body fluid environment, in the early stage, the composite biological scaffold materials can form a high-calcium environment favorable for the formation of new bone, and the calcium and magnesium ions are released continuously, which may support the potential osteogenic activity of the composite materials. The composite biological scaffold materials retain the exquisite three-dimensional interconnected mesh microstructure and the good mechanical strength of the bovine natural bone mineral, and at the same time, wispy whiskers with larger length-diameter ratio grow in the mesh, and the length-diameter ratio of the whisker is 8-25:1, which can increase the specific surface area of the materials and possibly improve the adhesion of cells. In the transplantation in the cancellous bone defect area of the animal bone, good adhesion, proliferation and differentiation of bone repair cells, and secretion of bone matrix by bone repair cells in the scaffold were observed; extremely early vascular formation was observed in the scaffold, and the osteogenesis process was similar to the intramembranous osteogenesis in physiological state. No obvious immunological rejection or inflammatory reaction was observed during the observation period, indicating that the composite biological scaffold materials have a good biocompatibility. The rapid and good bone repair in the bone defect area of the animal after being implanted with the composite biological scaffold materials also indicated the existence of the potential osteogenic activity of the composite biological scaffold materials.

Preferably, treating the calcined bovine cancellous bone mineral porous scaffold with the ternary system containing the magnesium source, the sulfur source and the phosphorus source is achieved by selecting one of the following solutions.

Solution 1: the calcined bovine cancellous bone mineral porous scaffold is first impregnated in a magnesium source solution, then taken out and dried, and then put into a sulfur source and phosphorus source composite solution to perform a hydrothermal reaction.

Solution 2: the calcined bovine cancellous bone mineral porous scaffold is subjected to a hydrothermal reaction while impregnated in a magnesium source, sulfur source, and phosphorus source composite solution.

Preferably, the hydrothermal reaction is carried out by a constant temperature hydrothermal method, the temperature is controlled at 70-90° C., and the reaction time is controlled for 8-36 h.

Preferably, in the solution 1, the solid-liquid ratio of the calcined bovine cancellous bone mineral porous scaffold to the magnesium source solution is 10 g: 50-200 mL, and the solid-liquid ratio of the calcined bovine cancellous bone mineral porous scaffold to the sulfur source and phosphorus source composite solution is 10 g: 50-200 mL.

Preferably, in the solution 2, the solid-liquid ratio of the calcined bovine cancellous bone mineral porous scaffold to the magnesium source, sulfur source, and phosphorus source composite solution is 10 g: 50-100 mL.

Preferably, the high-temperature calcination is performed at 750-900° C. for 2-9 h.

Preferably, the magnesium source is one or both of magnesium sulfate and magnesium hydrogen phosphate; the sulfur source is sulfuric acid and soluble sulfate, and the soluble sulfate is one or both of sodium sulfate and magnesium sulfate; and the phosphorus source is phosphoric acid and soluble phosphate, and the soluble phosphate is one selected from the group consisting of diammonium hydrogen phosphate, ammonium dihydrogen phosphate, magnesium hydrogen phosphate, a combination of magnesium hydrogen phosphate and diammonium hydrogen phosphate, and a combination of magnesium hydrogen phosphate and ammonium dihydrogen phosphate.

The magnesium sulfate in the magnesium source is both a source of magnesium ions and a source of sulfur; and the magnesium hydrogen phosphate in the magnesium source is both a source of magnesium ions and a source of phosphorus.

Preferably, a final concentration of the magnesium ions in the ternary system containing the magnesium source, the sulfur source and the phosphorus source is 0.05-0.2 mol/L.

Preferably, in the ternary system containing the magnesium source, the sulfur source and the phosphorus source, a final concentration of the sulfuric acid is 0.05-0.1 mol/L, and a final concentration of sulfate radicals provided by the sulfate is 0.04-0.6 mol/L. The sulfate radicals provided by the sulfate include sulfate radicals provided by the total sulfate in the magnesium source and the sulfur source.

Preferably, in the ternary system containing the magnesium source, the sulfur source and the phosphorus source, a final concentration of the phosphoric acid is 0.85-1.7 wt %, and a final concentration of the phosphorus provided by the phosphate is 0.08-0.9 mol/L. The phosphorus provided by the phosphate includes phosphorus provided by the total phosphate in the magnesium source and the phosphorus source. The phosphorus provided by the phosphate is derived from phosphate radical and/or hydrogen phosphate radical.

Preferably, the degradable magnesium-containing calcium phosphate-calcium sulfate porous composite biological scaffold has a material composition of one of the following composite components: calcium sulfate/magnesium-containing calcium phosphate, calcium sulfate/magnesium-containing calcium phosphate/hydroxyapatite, calcium sulfate/magnesium-containing calcium phosphate/hydroxyapatite/calcium pyrophosphate, calcium sulfate/magnesium-containing calcium phosphate/calcium pyrophosphate, calcium sulfate/poly (magnesium-containing calcium hydrogen phosphate), and calcium sulfate/poly (magnesium-containing calcium hydrogen phosphate)/hydroxyapatite.

Preferably, the calcined bovine cancellous bone mineral porous scaffold has a porosity of 70%-85% and an aperture of 400-1200 μm.

Preferably, the material of the degradable magnesium-containing calcium phosphate-calcium sulfate porous composite biological scaffold can be subjected to a gradient degradation. The degradable magnesium-containing calcium phosphate-calcium sulfate porous composite biological scaffold retains the three-dimensional interconnected mesh structure and the mechanical strength of the calcined bovine cancellous bone mineral porous scaffold, and at the same time, whiskers with larger length-diameter ratio grow in the mesh, and the length-diameter ratio of the whiskers is 8-25:1, which can effectively increase the specific surface area of the materials.

Preferably, a preparation method of the calcined bovine cancellous bone mineral porous scaffold is as follows:

(1) the bovine cancellous bone is cut into bone strips or bone blocks with a thickness of 0.5-1 cm to obtain raw bones;

(2) the raw bones are placed in distilled water and cooked in a pressure cooker for 40-60 min, then washed with 40-60° C. drinking water, this step is repeated 4-6 times; and (3) the processed raw bones obtained in the step (2) are dried in a constant temperature drying oven at 80-120° C. for 12-24 h, then placed in a calciner to be calcined at 900-1200° C. for 8-12 h, and cooled to obtain the calcined bovine cancellous bone mineral porous scaffold.

The present invention has the following beneficial effects.

In the present invention, the calcined bovine cancellous porous hydroxyapatite simple substance scaffold (calcined bovine cancellous bone mineral porous scaffold) can be stably and effectively transformed into degradable magnesium-containing calcium phosphate-calcium sulfate composite scaffold materials with various compositions, such as calcium sulfate/magnesium-containing calcium phosphate/hydroxyapatite, calcium sulfate/poly (magnesium-containing calcium hydrogen phosphate)/hydroxyapatite, calcium sulfate/magnesium-containing calcium phosphate, calcium sulfate/magnesium-containing calcium phosphate/calcium pyrophosphate/hydroxyapatite, calcium sulfate/magnesium-containing calcium phosphate/calcium pyrophosphate, etc. Osteogenic active ions including magnesium ions, sulfate ions, phosphorus ions, etc. are effectively added. Magnesium-containing component is magnesium-containing tricalcium phosphate or poly (magnesium-containing calcium hydrogen phosphate) with good degradation characteristics, the magnesium-containing component accounts for 9.5%-80% of the total mass of the material, and the molar percentage of the content of magnesium ions to the content of total cations is 0.5%-10%. The composite biological scaffold has calcium sulfate with relatively high degradation rate, potential osteoinductive active ions, and capable of being completely degraded. Calcium sulfate accounts for 7.2%-72.5% of the total mass of the composite material; some composite biological scaffolds further contain hydroxyapatite and/or calcium pyrophosphate. The composite biological scaffold material retains the three-dimensional interconnected mesh microstructure and the good mechanical strength of the natural bone mineral, and at the same time, whiskers with larger length-diameter ratio grow in the mesh, and the length-diameter ratio is 8-25:1, which can increase the specific surface area of the material, thus improving the adhesion of cells. Because of the obvious difference in the dissolution and degradation rates of the various components, the composite biological scaffold material can achieve gradient degradation. In addition, since the composition and mass ratio of the composite biological scaffold material can be effectively regulated according to the formula and production process, for example, under the experimental conditions, with the increase of the amount of sulfur, the content of calcium sulfate may be gradually increased without changing other conditions; with the increase of the amount of phosphorus, the hydroxyapatite with a calcium to phosphorus ratio of 1.67 is gradually converted into a magnesium-containing tricalcium phosphate with a (calcium and magnesium) to phosphorus ratio of approximately 1.5, and a calcium pyrophosphate with a calcium to phosphorus ratio of 1, the composition and mass ratio of the scaffold components can be effectively regulated, and therefore the effective regulation of the degradation rate of the composite biological scaffold material can be achieved. The degradation of calcium sulphate can form an early high-calcium environment, and the degradation of degradable magnesium-containing calcium phosphate such as magnesium-containing tricalcium phosphate and poly (magnesium-containing calcium hydrogen phosphate) can continuously release osteogenic active ions including magnesium ions and calcium ions, etc., which is conducive for the formation of new bone and provides further space for bone repair. The material still maintains good mechanical strength and mesh structure after a large proportion of dissolution and degradation, which can be confirmed in a dissolution and degradation test in simulated body fluid. The dissolution and degradation, and redeposition of the magnesium-doped calcium phosphate-calcium sulfate composite scaffolds were observed under electron microscope. When the degradable magnesium-containing calcium phosphate-calcium sulfate porous composite biological scaffold material of the present invention is transplanted in the bone defect area of the animal cancellous bone, good recruitment, adhesion, proliferation, differentiation, secretion of matrix, and rapid vascular formation of the repair cells were observed, and the material can achieve osteogenesis which is similar to the intramembranous osteogenesis in physiological state, indicating that the good osteoconductivity and the potential osteoinductive activity of the degradable magnesium-containing calcium phosphate-calcium sulfate porous composite biological scaffold. No obvious immunological rejection or inflammatory reaction was observed during the observation period, indicating that the degradable magnesium-containing calcium phosphate-calcium sulfate porous composite biological scaffold has a good biocompatibility.

In conclusion, the degradable magnesium-containing calcium phosphate-calcium sulfate porous composite biological scaffold materials have good three-dimensional interconnected mesh structure, osteoconductivity, degradability, good mechanical strength and biocompatibility, simultaneously. At the same time, nano calcium sulfate whiskers with larger length-diameter ratio grow in the mesh, which can increase the specific surface area of the material and possibly improve the adhesion of cells. The composite materials may have potential osteoinductivity due to the effective addition of the osteogenic active ionized magnesium and the calcium sulfate which can produce a local high-calcium environment when degraded. The degradable magnesium-containing calcium phosphate-calcium sulfate porous composite biological scaffold may more closely satisfy the ideal conditions for bone graft substitute materials or bone tissue engineering scaffold materials.

DETAILED DESCRIPTION OF THE EMBODIMENTS

Figure 1:
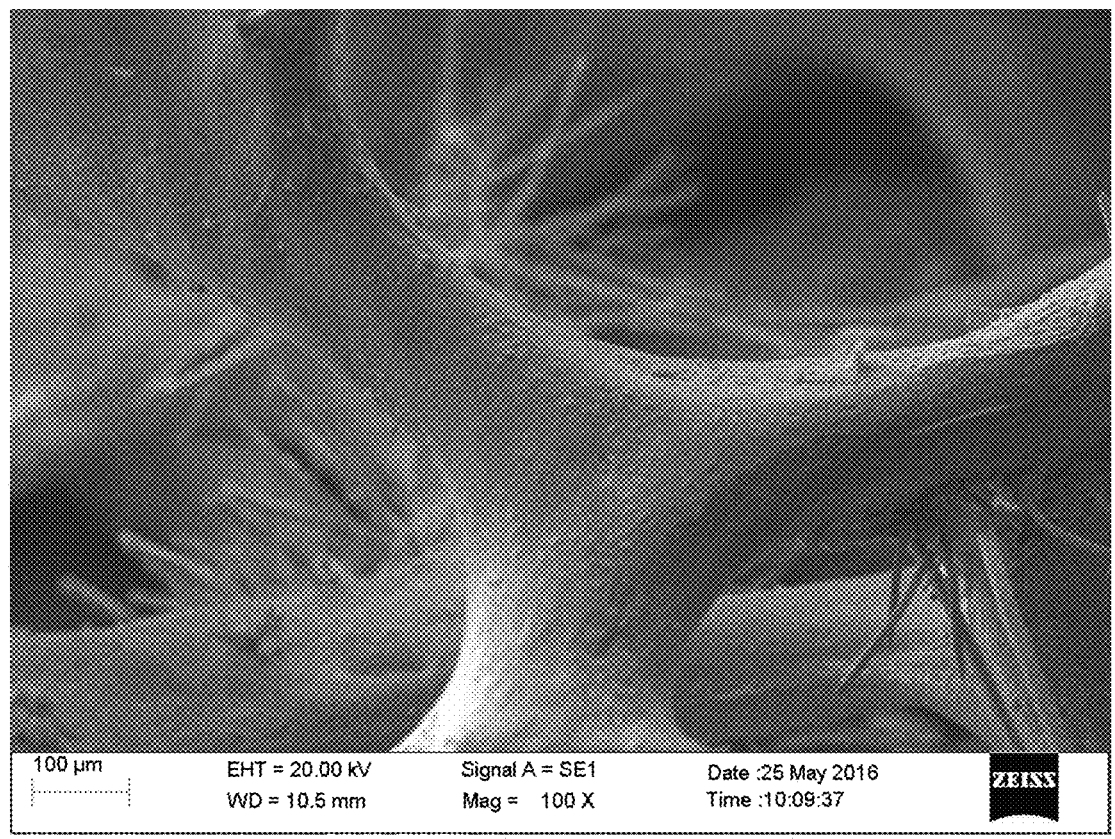
FIG. 1 is a scanning electron micrograph of a product of the present invention.

The technical solutions of the present invention will be further specifically described below with reference to specific embodiments.

In the present invention, the raw materials and equipment used, etc., are commercially available or commonly used in the art unless otherwise specified. The methods in the following embodiments, unless otherwise stated, are all conventional methods in the art.

Example 1 Preparation of Calcined Bovine Cancellous Bone Mineral Porous Scaffold (1) The bovine cancellous bone (cancellous bone from bovine femoral condyle) is cut into bone strips with a thickness of 0.5 cm to obtain raw bones;

(2) the raw bones are placed in distilled water and cooked in a pressure cooker for 40 min, then washed with 40° C. water, this step is repeated 6 times; and (3) the processed raw bones obtained in the step (2) are dried in a constant temperature drying oven at 80° C. for 24 h, then placed in a calciner to be calcined at 900° C. (a heating rate is 10° C./min) for 12 h, and cooled with the calciner to obtain the calcined bovine cancellous bone mineral porous scaffold.

Example 2 Preparation of Calcined Bovine Cancellous Bone Mineral Porous Scaffold (1) The bovine cancellous bone (cancellous bone from bovine femoral condyle) is cut into bone blocks with a thickness of 1 cm to obtain raw bones;

(2) the raw bones are placed in distilled water and cooked in a pressure cooker for 60 min, then washed with water at 60° C., this step is repeated 4 times; and (3) the processed raw bones obtained in the step (2) are dried in a constant temperature drying oven at 120° C. for 12 h, then placed in a calciner to be calcined at 1200° C. (a heating rate is 10° C./min) for 8 h, and cooled with the calciner to obtain the calcined bovine cancellous bone mineral porous scaffold.

Example 3 Preparation of Calcined Bovine Cancellous Bone Mineral Porous Scaffold (1) The bovine cancellous bone (cancellous bone from bovine femoral condyle) is cut into bone strips with a thickness of 0.8 cm to obtain raw bones;

(2) the raw bones are placed in distilled water and cooked in a pressure cooker for 50 min, then washed with 50° C. water, this step is repeated 5 times; and (3) the processed raw bones obtained in the step (2) are dried in a constant temperature drying oven at 100° C. for 18 h, then placed in a calciner to be calcined at 1000° C. (a heating rate is 10° C. imin) for 10 h, and cooled with the calciner to obtain the calcined bovine cancellous bone mineral porous scaffold.

General Implementation Solution 1:

A: The magnesium source, sulfur source, and phosphorus source composite solution is prepared: the phosphorus source is phosphoric acid and soluble phosphate, and the soluble phosphate is magnesium hydrogen phosphate, a combination of magnesium hydrogen phosphate and ammonium dihydrogen phosphate, a combination of magnesium hydrogen phosphate and diammonium hydrogen phosphate; the sulfur source is sulfuric acid and soluble sulfate, and the soluble sulfate is sodium sulfate; and the magnesium source is magnesium hydrogen phosphate.

In the composite solution: a final concentration of phosphoric acid is 0.85-1.7 wt %, a final concentration of phosphorus provided by the phosphate (soluble phosphate and magnesium source) is 0.1-0.9 mol/L, a concentration of sulfuric acid is 0.05-0.1 mol/L, and the soluble sulfate is sodium sulfate, a final concentration of sulfate radicals provided by the sulfate is 0.08-0.6 mol/L; a final concentration of magnesium ion is 0.05-0.2 mol/L.

According to the solid-liquid ratio of the calcined bovine cancellous bone mineral porous scaffolds to the magnesium source, sulfur source, and phosphorus source composite solution of 10 g: 50-100 mL, the calcined bovine cancellous bone mineral porous scaffolds are weighed, and then put into the magnesium source, sulfur source, and phosphorus source composite solution to be subjected to impregnation and hydrothermal reaction. The hydrothermal reaction is a constant temperature hydrothermal reaction, the reaction temperature is controlled at 70-90° C., and the reaction time is controlled for 8-36 h.

B: The porous scaffolds are taken out, and placed in a constant temperature drying oven and dried at 80-90° C. for 20-48 h.

C: The processed calcined bovine cancellous bone mineral porous scaffolds obtained in the step B are placed in a calciner to be calcined at 750-900° C. (a heating rate is 2.5° C. imin) for 2-8 h, and cooled with the calciner to obtain the degradable magnesium-containing calcium phosphate-calcium sulfate porous composite biological scaffolds.

General Implementation Solution 2:

A: The magnesium source, sulfur source, and phosphorus source composite solution is prepared: the phosphorus source is phosphoric acid and soluble phosphate, and the soluble phosphate is magnesium hydrogen phosphate, or diammonium hydrogen phosphate; the sulfur source is sulfuric acid and soluble sulfate, and the soluble sulfate is magnesium sulfate, or a combination of magnesium sulfate and sodium sulfate; the magnesium source is magnesium sulfate, or a combination of magnesium sulfate and magnesium hydrogen phosphate.

In the composite solution: a final concentration of phosphoric acid is 0.85-1.7 wt %, a final concentration of phosphorus provided by the phosphate is 0.1-0.8 mol/L, a concentration of sulfuric acid is 0.05-0.1 mol/L, and the soluble sulfate is magnesium sulfate, or a combination of magnesium sulfate and sodium sulfate, a final concentration of sulfate radicals provided by the sulfate is 0.08-0.6 mol/L; a final concentration of magnesium ions is 0.05-0.15 mol/L.

B: The magnesium sulfate is first weighed for preparing a magnesium sulfate solution, and the solid-liquid ratio of the calcined bovine cancellous bone mineral porous scaffolds to the magnesium sulfate solution is 10 g: 50-200 mL; subsequently, the calcined bovine cancellous bone mineral porous scaffolds are impregnated into the magnesium sulfate solution for 15-30 min; and then a microwave drying is performed, the microwave output power is 300-500 W, and the drying time is 15-24 min.

C: A sulfur source and phosphorus source composite solution is prepared according to the solid-liquid ratio of the calcined bovine cancellous bone mineral porous scaffolds to the sulfur source and phosphorus source composite solution of 10 g: 50-200 mL; and the processed calcined bovine cancellous bone mineral porous scaffolds obtained in the step B are subjected to impregnation and hydrothermal reaction. The hydrothermal reaction is a constant temperature hydrothermal reaction, the reaction temperature is controlled at 70-90° C., and the reaction time is controlled for 12-36 h.

D: The porous scaffolds are taken out, and placed in a constant temperature drying oven and dried at 80-90° C. for 20-48 h.

E: The processed calcined bovine cancellous bone mineral porous scaffolds obtained in the step D are placed in a calciner to be calcined at 750-900° C. (a heating rate is 2.5° C./min) for 2-9 h, and cooled with the calciner to obtain the degradable magnesium-containing calcium phosphate-calcium sulfate porous composite biological scaffolds.

Each sample is observed in general and subjected to X-ray diffraction (XRD) analysis. Some samples are selected and subjected to microstructure observation under a scanning electron microscopy (SEM), dissolution and degradation tests in simulated body fluid, and animal experiments about bone defect repair. The shape and strength of the materials are observed generally; and some samples are tested for compressive strength using an INSTRON-5566 universal testing machine. Medical sodium chloride injection is used as the simulated body fluid in the dissolution and degradation test in simulated body fluid. The solid-liquid ratio (mass to volume ratio) of the test material to the simulated body fluid is 1 g: 100 ml. The test material and the simulated body fluid are placed in a beaker having a cover, and the dissolution and degradation test in the simulated body fluid is performed under constant temperature condition of 37° C. The dissolution and degradation test duration is 30 days. Calcium ion, phosphorus ion and magnesium ion in the simulated body fluid are detected by AU5800 automatic biochemical analyzer every 4 days. In the first 15 days of the dissolution and degradation, 40% of the simulated body fluid is replaced every 3 days, and the simulated body fluid is not replaced in the later period. After 30 days of the dissolution and degradation test, the mass of the sample is measured by a domestic electronic balance and the degradation rate is calculated. XRD analysis and SEM observation of the materials are performed before and at the end of the dissolution and degradation test. In the animal bone defect repair test, forty-eight of healthy New Zealand white rabbits were selected, and bone defects having diameters of 8 mm were made in the femoral condyles of the rabbits. The rabbits were randomly divided into experimental group (porous composite biomaterials) and control group (imported synthetic calcium-phosphorus materials). The same artificial bone defect was made to the rabbits in the experimental group and the control group, respectively. Then, the rabbits in the experimental group were treated with porous composite biomaterials for repairing the bone defect; and the rabbits in the control group were treated with imported synthetic calcium-phosphorus bone substitute materials for repairing the bone defect. The experimental animals were sacrificed 1, 2, 4 and 8 weeks after the surgery for histological examination of bone defect repair.

Embodiment 1

10 ml of 1 mol/L sulfuric acid, 4.26 g sodium sulfate, 1.74 g magnesium hydrogen phosphate, and 2 ml of 85 wt % phosphoric acid stock solution are taken, and added into deionized water to prepare 100 ml of composite solution containing 0.1 mol/L sulfuric acid, 0.3 mol/L sodium sulfate, 0.1 mol/L magnesium hydrogen phosphate and 1.7 wt % phosphoric acid; and the pH of the composite solution is about 2.5. 10 g of calcined bovine cancellous bone mineral porous scaffold is impregnated in the composite solution and subjected to impregnation and hydrothermal reaction for 20 h at a constant temperature of 70° C., and is covered by an inversely beaker. Then, the calcined bovine cancellous bone mineral porous scaffold is taken out, and dried at 80° C. for 24 h, then calcined in a calciner where the temperature is raised to 750° C. at a heating rate of 2.5° C. imin and maintained at 750° C. for 6 h, and cooled with the calciner to room temperature to obtain 511035E.
511035E

| | |
|---|---|
| $CaSO_4$ | 33.33% |
| $Ca_{2.89}Mg_{0.11}(PO_4)_2$ | 33.16% |
| $Ca_{9.74}(PO_4)_6(OH)_{2.08}$ | 33.51%. |

Embodiment 2

511036

10 ml of 1 mol/L sulfuric acid, 4.26 g sodium sulfate, 3.46 g magnesium hydrogen phosphate, and 2 ml of 85 wt % phosphoric acid are taken, and added into deionized water to prepare 100 ml of composite solution containing 0.1 mol/L sulfuric acid, 0.3 mol/L sodium sulfate, 0.2 mol/L magnesium hydrogen phosphate and 1.7 wt % phosphoric acid, a pH of the composite solution is about 3.0. 10 g of calcined bovine cancellous bone mineral porous scaffold is impregnated in the composite solution and subjected to impregnation and hydrothermal reaction for 20 h at a constant temperature of 70° C., and is covered by an inversely beaker. Then, the calcined bovine cancellous bone mineral porous scaffold is taken out, and dried at 80° C. for 24 h, then calcined in a calciner where the temperature is raised to 750° C. at a heating rate of 2.5° C./min and maintained at 750° C. for 6 h, and cooled with the calciner to room temperature to obtain 511036E.
511036E

| | |
|---|---|
| $CaSO_4$ | 26.23% |
| $Ca_{18}Mg_2H_2(PO_4)_{14}$ | 59.97% |
| $Ca_5(PO_4)OH$ | 13.80%. |

Embodiment 3

511135

5 ml of 1 mol/L sulfuric acid, 1.12 g sodium sulfate, 1.70 g magnesium hydrogen phosphate, and 1 ml of 85 wt %/o phosphoric acid are taken, and added into deionized water to prepare 100 ml of composite solution containing 0.05 mol/L sulfuric acid, 0.08 mol/L sodium sulfate, 0.1 mol/L magnesium hydrogen phosphate and 0.85 wt % phosphoric acid, a pH of the composite solution is about 3-3.5. 10 g of calcined bovine cancellous bone mineral porous scaffold is impregnated in the composite solution and subjected to impregnation and hydrothermal reaction for 8 h at a constant temperature of 90° C., and is covered by an inversely beaker. Then, the calcined bovine cancellous bone mineral porous scaffold is taken out, and dried at 80° C. for 24 h, a weight of the calcined bovine cancellous bone mineral porous scaffold after drying is 11.93 g, then calcined in a calciner where the temperature is raised to 900° C. at a heating rate of 2.5° C./min and maintained at 900° C. for 8 h, and cooled with the calciner to room temperature to obtain 511135M.
511135M

| | |
|---|---|
| $CaSO_4$ | 20.01% |
| $Ca_{2.71}Mg_{0.29}H_2(PO_4)_2$ | 45.57% |
| $Ca_{2.89}Mg_{0.11}(PO_4)_2$ | 34.42%. |

Embodiment 4

601052

2.5 ml of 1 mol/L sulfuric acid, 4.26 g sodium sulfate, 1 ml of 85 wt % phosphoric acid, 5.28 g diammonium hydrogen phosphate, and 0.86 g magnesium hydrogen phosphate are taken, and added into deionized water to prepare 50 ml of composite solution containing 0.05 mol/L sulfuric acid, 0.3 mol/L sodium sulfate, 0.85 wt % phosphoric acid, 0.8 mol/L diammonium hydrogen phosphate and 0.1 mol/L magnesium hydrogen phosphate. 10 g of calcined bovine cancellous bone mineral porous scaffold is impregnated in the composite solution and subjected to impregnation and hydrothermal reaction for 24 h at a constant temperature of 90° C., and is covered by an inversely beaker. Then, the calcined bovine cancellous bone mineral porous scaffold is taken out, and dried at 100° C. for 24 h, then calcined in a calciner where the temperature is raised to 750° C. at a heating rate of 2.5° C./min and maintained at 750° C. for 2 h, and cooled with the calciner to room temperature to obtain 601052A; and the calcined bovine cancellous bone mineral porous scaffold after being subjected to drying is calcined in the calciner where the temperature is raised to 750° C. at a heating rate of 2.5° C./min and maintained at 750° C. for 5 h, and cooled with the calciner to room temperature to obtain 601052E.

601052A

| | |
|---|---|
| $CaSO_4$ | 20.46% |
| $(Ca_{2.589}Mg_{0.411})(PO_4)_2$ | 19.17% |
| $Ca_2(P_2O_7)$ | 37.88% |
| $Ca_{10.042}(PO_4)_{5.952}(OH)_{2.292}$ | 22.50%. |

601052E

| | |
|---|---|
| $CaSO_4$ | 29.36% |
| $(Ca_{2.589}Mg_{0.411})(PO_4)_2$ | 19.64% |
| $Ca_2(P_2O_7)$ | 28.05% |
| $Ca_{10.042}(PO_4)_{5.952}(OH)_{2.292}$ | 22.94%. |

Embodiment 5

601053

5 ml of 1 mol/L sulfuric acid, 2.84 g sodium sulfate, 1 ml of 85 wt % phosphoric acid solution, 2.64 g diammonium hydrogen phosphate, and 1.72 g magnesium hydrogen phosphate are taken, and added into deionized water to prepare 50 ml of composite solution containing 0.1 mol/L sulfuric acid, 0.2 mol/L sodium sulfate, 0.85 wt % phosphoric acid, 0.4 mol/L diammonium hydrogen phosphate and 0.2 mol/L magnesium hydrogen phosphate. 6 g of calcined bovine cancellous bone mineral porous scaffold is impregnated in the composite solution and subjected to impregnation and hydrothermal reaction for 36 h at a constant temperature of 90° C. Then, the calcined bovine cancellous bone mineral porous scaffold is taken out, and dried at 100° C. for 24 h, then calcined in a calciner where the temperature is raised to 750° C. at a heating rate of 2.5° C. imin and maintained at 750° C. for 2 h, and cooled with the calciner to room temperature to obtain 601053A; and the calcined bovine cancellous bone mineral porous scaffold after being subjected to drying is calcined in the calciner where the temperature is raised to 750° C. at a heating rate of 2.5° C./min and maintained at 750° C. for 5 h, and cooled with the calciner to room temperature to obtain 601053E.

601053A

| | |
|---|---|
| $CaSO_4$ | 18.25% |
| $(Ca_{2.589}Mg_{0.411})(PO_4)_2$ | 13.45% |
| $Ca_2(P_2O_7)$ | 19.38% |
| $Ca_{10.042}(PO_4)_{5.952}(OH)_{2.292}$ | 48.92%. |

| | |
|---|---|
| $CaSO_4$ | 21.03% |
| $(Ca_{2.589}Mg_{0.411})(PO_4)_2$ | 28.22% |
| $Ca_2(P_2O_7)$ | 27.63% |
| $Ca_{10.042}(PO_4)_{5.952}(OH)_{2.292}$ | 24.15%. |

Embodiment 6

511033

10 ml of 1 mol/L sulfuric acid, 4.26 g sodium sulfate, 0.86 g magnesium hydrogen phosphate, 5.78 g ammonium dihydrogen phosphate, and 2 ml of 85 wt % phosphoric acid are taken, and added into deionized water to prepare 100 ml of composite solution containing 0.1 mol/L sulfuric acid, 0.3 mol/L sodium sulfate, 0.05 mol/L magnesium hydrogen phosphate, 1.7 wt % phosphoric acid and 0.5 mol/L ammonium dihydrogen phosphate. 10 g of calcined bovine cancellous bone mineral porous scaffold is impregnated in the composite solution and subjected to impregnation and hydrothermal reaction for 20 h at a constant temperature of 70° C., and is covered by an inversely beaker. Then, the calcined bovine cancellous bone mineral porous scaffold with a pH of about 2.5 is taken out, and dried at 80° C. for 24 h, then calcined in a calciner where the temperature is raised to 750° C. at a heating rate of 2.5° C./min and maintained at 750° C. for 6 h, and cooled with the calciner to room temperature to obtain 511033E.

511033E

| | |
|---|---|
| $CaSO_4$ | 37.97% |
| $Ca_{2.86}Mg_{0.14}(PO_4)$ | 28.90% |
| $Ca_2(P_2O_7)$ | 53.13%. |

Embodiment 7

511034

5 ml of 1 mol/L sulfuric acid, 1.43 g sodium sulfate, 0.87 g magnesium hydrogen phosphate, 5.78 g ammonium dihydrogen phosphate, and 2 ml of 85 wt % phosphoric acid stock solution are taken, and added into deionized water to prepare 100 ml of composite solution containing 0.05 mol/L sulfuric acid, 0.1 mol/L sodium sulfate, 0.1 mol/L magnesium hydrogen phosphate, 0.5 mol/L ammonium dihydrogen phosphate, and 1.7 wt % phosphoric acid; and the pH of the composite solution is about 2.5. 10 g of calcined bovine cancellous bone mineral porous scaffold is impregnated in the composite solution and subjected to impregnation and hydrothermal reaction for 20 h at a constant temperature of 70° C., and is covered by an inversely beaker. Then, the calcined bovine cancellous bone mineral porous scaffold is taken out, and dried at 80° C. for 24 h, then calcined in a calciner where the temperature is raised to 750° C. at a heating rate of 2.5° C. imin and maintained at 750° C. for 6 h, and cooled with the calciner to room temperature to obtain 511034E.

511034E

| | |
|---|---|
| $CaSO_4$ | 7.2% |
| $Ca_{2.89}Mg_{0.11}(PO_4)_2$ | 27.03% |
| $Ca_2(P_2O_7)$ | 64.17%. |

Embodiment 8

602124

According to the amount of solution required for hydrothermal reaction, 0.1 mol/L magnesium sulfate hexahydrate, and a composite solution containing 1.7 wt % phosphoric acid, 0.1 mol/L sulfuric acid and 0.4 mol/L diammonium hydrogen phosphate are prepared, for this purpose, 1.2 g of magnesium sulfate hexahydrate, 1 ml of phosphoric acid, 5 ml of sulfuric acid and 2.64 g of diammonium hydrogen phosphate are taken. First, 50 ml of magnesium-containing solution is prepared with 1.2 g magnesium sulfate; and 5 g of calcined bovine cancellous bone mineral porous scaffold is impregnated in the magnesium-containing solution, then dried with microwave, and taken out. 5 ml of 1 mol/L sulfuric acid, 1 ml of 85 w % phosphoric acid, and 2.64 g diammonium hydrogen phosphate are taken, and added into deionized water to prepare 50 ml of the composite solution; then the calcined bovine cancellous bone mineral porous scaffold after being subjected to impregnating in the magnesium-containing solution is impregnated in the composite solution and reacted at 70° C. for 36 h. Then, the calcined bovine cancellous bone mineral porous scaffold is taken out, and dried at 70° C. for 30 h, a weight of the calcined bovine cancellous bone mineral porous scaffold after drying is 5.89 g, then calcined in a calciner where the temperature is raised to 750° C. at a heating rate of 2.5° C. imin and maintained at 750° C. for 6 h, and cooled with the calciner to room temperature to obtain 602124E; and the calcined bovine cancellous bone mineral porous scaffold after being subjected to drying is calcined in the calciner where the temperature is raised to 750° C. at a heating rate of 2.5° C./min and maintained at 750° C. for 9 h, and cooled with the calciner to room temperature to obtain 602124K. The permeability, strength and appearance are good.

602124E

| | |
|---|---|
| $CaSO_4$ | 36.4% |
| $(Ca_{2.589}Mg_{0.411})(PO_4)_2$ | 10.5% |
| $Ca_{10.042}(PO_4)_{5.952}(OH)_{2.292}$ | 53.1%. |

602124K

| | |
|---|---|
| $CaSO_4$ | 54.8% |
| $(Ca_{2.589}Mg_{0.411})(PO_4)_2$ | 11.4% |
| $Ca_{10.042}(PO_4)_{5.952}(OH)_{2.292}$ | 33.8%. |

Embodiment 9

602123

According to the amount of solution required for hydrothermal reaction, 0.1 mol/L magnesium sulfate hexahydrate, and a composite solution containing 1.7 wt % phosphoric acid, 0.1 mol/L sulfuric acid and 0.2 mol/L diammonium hydrogen phosphate are prepared, for this purpose, 1.2 g of magnesium sulfate hexahydrate, 1 ml of phosphoric acid, 5 ml of sulfuric acid and 1.32 g of diammonium hydrogen phosphate are taken. First, 50 ml of magnesium-containing solution is prepared with 1.2 g magnesium sulfate; and 5 g of calcined bovine cancellous bone mineral porous scaffold is impregnated in the magnesium-containing solution, then dried with microwave, and taken out. 5 ml of 1 mol/L sulfuric acid, 1 ml of 85 w % phosphoric acid, and 1.32 g diammonium hydrogen phosphate are taken, and added into deionized water to prepare 50 ml of the composite solution; then the calcined bovine cancellous bone mineral porous scaffold after being subjected to impregnating in the magnesium-containing solution is impregnated in the composite solution and reacted at 70° C. for 36 h. Then, the calcined bovine cancellous bone mineral porous scaffold is taken out, and dried at 70° C. for 30 h, a weight of the calcined bovine cancellous bone mineral porous scaffold after drying is 5.68 g, then calcined in a calciner where the temperature is raised to 750° C. at a heating rate of 2.5° C./min and maintained at 750° C. for 3 h, and cooled with the calciner to room temperature to obtain 602123A; the calcined bovine cancellous bone mineral porous scaffold after being subjected to drying is calcined in the calciner, where the temperature is raised to 750° C. at a heating rate of 2.5° C./min and maintained at 750° C. for 6 h, and cooled with the calciner to room temperature to obtain 602123E; and the calcined bovine cancellous bone mineral porous scaffold after being subjected to drying is calcined in the calciner, where the temperature is raised to 750° C. at a heating rate of 2.5° C./min and maintained at 750° C. for 9 h, and cooled with the calciner to room temperature to obtain 602123K.

602123A

| | |
|---|---|
| $CaSO_4$ | 39.79% |
| $(Ca_{2.589}Mg_{0.411})(PO_4)_2$ | 9.82% |
| $Ca_{9.74}(PO_4)_6(OH)_{2.08}$ | 50.39%. |

602123E

| | |
|---|---|
| $CaSO_4$ | 37.7% |
| $Ca_{2.71}Mg_{0.29}(PO_4)_2$ | 11.3% |
| $Ca_{9.74}(PO_4)_6(OH)_{2.08}$ | 51.0%. |

602123K

| | |
|---|---|
| $CaSO_4$ | 65.2% |
| $(Ca_{2.589}Mg_{0.411})(PO_4)_2$ | 9.5% |
| $Ca_{10.042}(PO_4)_{5.952}(OH)_{2.292}$ | 25.3%. |

Embodiment 10

602122

According to the amount of solution required for hydrothermal reaction, 0.15 mol/L magnesium sulfate hexahydrate, and a composite solution containing 1.7 wt % phosphoric acid, 0.1 mol/L sulfuric acid, 0.375 mol/L sodium sulfate and 0.2 mol/L diammonium hydrogen phosphate are prepared, for this purpose, 1.8 g of magnesium sulfate hexahydrate, 1 ml of 85 wt % phosphoric acid, 5 ml of sulfuric acid, 2.13 g of sodium sulfate and 1.32 g of diammonium hydrogen phosphate are taken. First, 50 ml of magnesium-containing solution is prepared with 1.8 g magnesium sulfate; and 5 g of calcined bovine cancellous bone mineral porous scaffold is impregnated in the magnesium-containing solution, dried with microwave, and taken out. 5 ml of 1 mol/L sulfuric acid, 2.13 g sodium sulfate, 1 ml of 85 w % phosphoric acid, and 1.32 g diammonium hydrogen phosphate are taken, and added into deionized water to prepare 50 ml of the composite solution of sulfuric acid, sodium sulfate, phosphoric acid and diammonium hydrogen phosphate; then, the calcined bovine cancellous bone mineral porous scaffold after being subjected to impregnating in the magnesium-containing solution is impregnated in the composite solution to be subjected to impregnation and hydrothermal reaction at 70° C. for 36 h. Then, the calcined bovine cancellous bone mineral porous scaffold is taken out, and dried at 70° C. for 30 h, a weight of the calcined bovine cancellous bone mineral porous scaffold after being subjected to drying is 6.12 g, then calcined in a calciner where the temperature is raised to 750° C. at a heating rate of 2.5°

C./min and maintained at 750° C. for 6 h, and cooled with the calciner to room temperature to obtain 602122E; and the calcined bovine cancellous bone mineral porous scaffold after being subjected to drying is calcined in the calciner, where the temperature is raised to 750° C. at a heating rate of 2.5° C./min and maintained at 750° C. for 9 h, and cooled with the calciner to room temperature to obtain 602122K.

602122E

| | |
|---|---|
| $CaSO_4$ | 53.5% |
| $(Ca_{2.589}Mg_{0.411})(PO_4)_2$ | 14.8% |
| $Ca_{10.042}(PO_4)_{5.952}(OH)_{2.292}$ | 31.7%. |

602122K

| | |
|---|---|
| $CaSO_4$ | 44.5% |
| $(Ca_{2.589}Mg_{0.411})(PO_4)_2$ | 16.3% |
| $Ca_{9.74}(PO_4)_6(OH)_{2.08}$ | 39.2%. |

Embodiment 11

602121

According to the amount of solution required for hydrothermal reaction, 0.1 mol/L magnesium sulfate hexahydrate, and a composite solution containing 1.7 wt % phosphoric acid, 0.1 mol/L sulfuric acid, 0.5 mol/L sodium sulfate and 0.4 mol/L diammonium hydrogen phosphate are prepared, for this purpose, 1.2 g of magnesium sulfate hexahydrate, 1 ml of 85 wt % phosphoric acid, 5 ml of sulfuric acid, 2.84 g of sodium sulfate and 1.32 g of diammonium hydrogen phosphate are taken. First, 1.2 g of magnesium sulfate hexahydrate is taken and added into deionized water to prepare 50 ml of magnesium sulfate solution; and 5 g of calcined bovine cancellous bone mineral porous scaffold with a porosity of about 85% is impregnated in the magnesium sulfate solution for 30 min, dried with microwave, and taken out. 5 ml of 1 mol/L sulfuric acid, 2.84 g sodium sulfate, 1 ml of 85 wt % phosphoric acid, and 2.64 g diammonium hydrogen phosphate are taken to prepare 50 ml of the composite solution containing sulfuric acid, 0.1 mol/L sodium sulfate, 1.7 wt % phosphoric acid and diammonium hydrogen phosphate; then, the calcined bovine cancellous bone mineral porous scaffold after being subjected to impregnating in the magnesium sulfate solution is impregnated in the composite solution to be subjected to impregnation and hydrothermal reaction for 36 h at a constant temperature of 90° C., and is covered by an inversely beaker. Then, the calcined bovine cancellous bone mineral porous scaffold is taken out, and dried at 70° C. for 30 h, a weight of the calcined bovine cancellous bone mineral porous scaffold after being subjected to drying is 6.18 g, and the calcined bovine cancellous bone mineral porous scaffold after being subjected to drying has good permeability, good strength, good appearance and appears to have whisker formation. The calcined bovine cancellous bone mineral porous scaffold after being subjected to drying is calcined in a calciner where the temperature is raised to 750° C. at a heating rate of 2.5° C./min and maintained at 750° C. for 6 h, and cooled with the calciner to room temperature to obtain 602121E; and the calcined bovine cancellous bone mineral porous scaffold after being subjected to drying is calcined in the calciner, where the temperature is raised to 750° C. at a heating rate of 2.5° C./min and maintained at 750° C. for 9 h, and cooled with the calciner to room temperature to obtain 602121K.

602121E

| | |
|---|---|
| $CaSO_4$ | 29.6% |
| $(Ca_{2.589}Mg_{0.411})(PO_4)_2$ | 23.8% |
| $Ca_{10.042}(PO_4)_{5.952}(OH)_{2.292}$ | 46.6%. |

602121K

| | |
|---|---|
| $CaSO_4$ | 39.0% |
| $Ca_{18}Mg_2H_2(PO_4)_{14}$ | 22.2% |
| $Ca_{9.74}(PO_4)_6(OH)_{2.08}$ | 38.8%. |

Embodiment 12

603292

According to the amount of solution required for hydrothermal reaction, 0.05 mol/L magnesium sulfate hexahydrate, and a composite solution containing 1.7 wt % phosphoric acid, 0.1 mol/L sulfuric acid, 0.2 mol/L sodium sulfate and 0.1 mol/L magnesium hydrogen phosphate are prepared, for this purpose, 0.6 g of magnesium sulfate hexahydrate, 2 ml of 85 wt % phosphoric acid, 5 ml of sulfuric acid, 2.23 g of sodium sulfate and 1.74 g of magnesium hydrogen phosphate are taken. First, 0.6 g of magnesium sulfate hexahydrate is taken to prepare 100 ml of magnesium sulfate solution; and 5 g of calcined bovine cancellous bone mineral porous scaffold with a porosity of about 85% is put into the magnesium sulfate solution for impregnation for 30 min, dried at 500 W microwave for 10×3 min, and taken out. 5 ml of 1 mol/L sulfuric acid, 2.23 g sodium sulfate, 1.74 g magnesium hydrogen phosphate, and 2 ml of 85 w % phosphoric acid are used to prepare 100 ml of the composite solution containing sulfuric acid, sodium sulfate, magnesium hydrogen phosphate and phosphoric acid with a pH of 3.5; the calcined bovine cancellous bone mineral porous scaffold after being subjected to impregnating in the magnesium sulfate solution is impregnated in the composite solution to be subjected to impregnation and hydrothermal reaction for 12 h at a constant temperature of 90° C., and is covered by an inversely beaker. Then, the calcined bovine cancellous bone mineral porous scaffold is taken out, and dried at 90° C. for 24 h, and then calcined in a calciner where the temperature is raised to 900° C. at a heating rate of 2.5° C. imin and maintained at 900° C. for 8 h, and cooled with the calciner to room temperature to obtain 603292E.

603292E

| | |
|---|---|
| $CaSO_4$ | 51.1% |
| $(Ca_{2.89}Mg_{0.11})(PO_4)_2$ | 48.9% |

Embodiment 13

603294

0.6 g of magnesium sulfate hexahydrate is taken and added into deionized water to prepare 60 ml of magnesium sulfate solution; and 5 g of calcined bovine cancellous bone mineral porous scaffold with a porosity of about 85% is put into the magnesium sulfate solution for impregnation for 30 min, dried at 500 W microwave for 8×3 min, and taken out. 5 ml of 1 mol/L sulfuric acid, 1 ml of 85 w % phosphoric acid, and 0.86 g magnesium hydrogen phosphate are taken, and added into deionized water to prepare 60 ml of composite solution; the calcined bovine cancellous bone mineral porous scaffold after being subjected to impregnating in the magnesium sulfate solution is impregnated in the composite solution and to be subjected to impregnation and hydrothermal reaction for 24 h at a constant temperature of 70° C. Then, the calcined bovine cancellous bone mineral porous scaffold is taken out, and dried at 90° C. for 24 h, and then calcined in a calciner where the temperature is raised to 900° C. at a heating rate of 2.5° C./min and maintained at 900° C. for 6 h, and cooled with the calciner to room temperature to obtain 603294E.
603294E

| | |
|---|---|
| $CaSO_4$ | 72.5% |
| $(Ca_{2.89}Mg_{0.11})(PO_4)_2$ | 27.5%. |

Embodiment 14

603295

0.6 g of magnesium sulfate hexahydrate is taken and added into deionized water to prepare 60 ml of magnesium sulfate solution; and 5 g of calcined bovine cancellous bone mineral porous scaffold with a porosity of about 85% is put into the magnesium sulfate solution for impregnation for 30 min, dried at a microwave output power of 500 W for 8×3 min, and taken out. 5 ml of 1 mol/L sulfuric acid, 1 ml of 85 w % phosphoric acid, 1.72 g magnesium hydrogen phosphate are taken to prepare 60 ml of composite solution; then the calcined bovine cancellous bone mineral porous scaffold is put in the composite solution and subjected impregnation and hydrothermal reaction for 24 h at a constant temperature of 70° C. Then, the calcined bovine cancellous bone mineral porous scaffold is taken out, and dried at 70° C. for 30 h, the calcined bovine cancellous bone mineral porous scaffold after being subjected to drying has general strength and general permeability. The calcined bovine cancellous bone mineral porous scaffold after being subjected to drying is calcined in the calciner where the temperature is raised to 900° C. at a heating rate of 2.5° C./min and maintained at 900° C. for 6 h, and cooled with the calciner to room temperature to obtain 603295E.
603295E

| | |
|---|---|
| $CaSO_4$ | 70.2% |
| $(Ca_{2.89}Mg_{0.11})(PO_4)_2$ | 29.8%. |

1. Testing Results:

The general observation, strength measurement, XRD component analysis and SEM observation of the materials show that the prefabricated form of the bovine cancellous bone is well retained in all kinds of products, without fragmentation, collapse or powdering, and the products have good mechanical strength. The compressive strengths of the cancellous bones from specimens Nos. 1-5 having a size of 10×10×10 mm were tested using the INSTRON-5566 universal testing machine and the results are shown in Tab. 1. The X-ray diffraction (XRD) test confirms that the calcined bovine cancellous bone mineral scaffold, impregnated with magnesium sulfate, subjected to hydrothermal reaction in a sulfur source and phosphorus source composite solution, and after drying and calcination, can be converted into degradable magnesium-doped calcium phosphate-calcium sulfate porous composite biological scaffold materials, such as the compounds of calcium sulfate/magnesium-containing calcium phosphate, calcium sulfate/magnesium-containing calcium phosphate/hydroxyapatite, calcium sulfate/magnesium-containing calcium phosphate/hydroxyapatite/calcium pyrophosphate, calcium sulfate/magnesium-containing calcium phosphate/calcium pyrophosphate, calcium sulfuric/poly (magnesium-containing calcium hydrogen phosphate), etc. Magnesium-containing calcium phosphate is magnesium-containing tricalcium phosphate or poly (magnesium-containing calcium hydrogen phosphate) with good degradation characteristics. The molar percentage of the content of magnesium ions to the content of total cations is 0.5%-10%, the magnesium-containing component such as magnesium-containing tricalcium phosphate or poly (magnesium-containing calcium hydrogen phosphate) accounts for 9.6%-72.5% of the total mass of the material, and calcium sulfate accounts for 8%-72.5% of the total mass of the material.

The scanning electron microscopy (referring to FIG. 1) shows that the products have retained the main structure of the three-dimensional interconnected mesh microstructure of the natural bone mineral of the bovine cancellous bone, and at the same time, calcium sulfate whiskers with larger length-diameter ratio grow in the mesh, which can increase the specific surface area of the materials and possibly improve the adhesion of cells.

TABLE 1

| Compressive strength | |
|---|---|
| No. | compressive strength (MPa) |
| 1 | 8.40 |
| 2 | 6.35 |
| 3 | 13.79 |
| 4 | 11.46 |

2. In-Vitro Dissolution and Degradation Test of Materials

Figure 2:
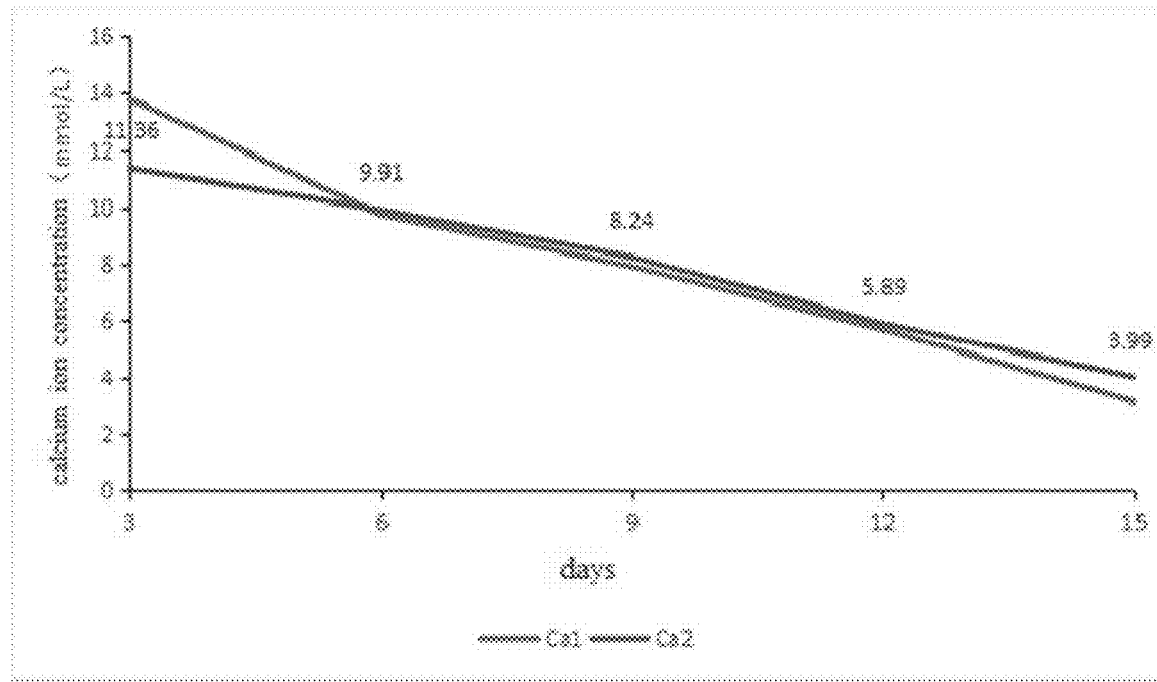
FIG. 2 is a diagram showing a calcium value of a product of the present invention in an early stage of a dissolution and degradation test in simulated body fluid (n=3, the reference value of human serum calcium ion is 2-2.67 mmol/L).
Figure 3:
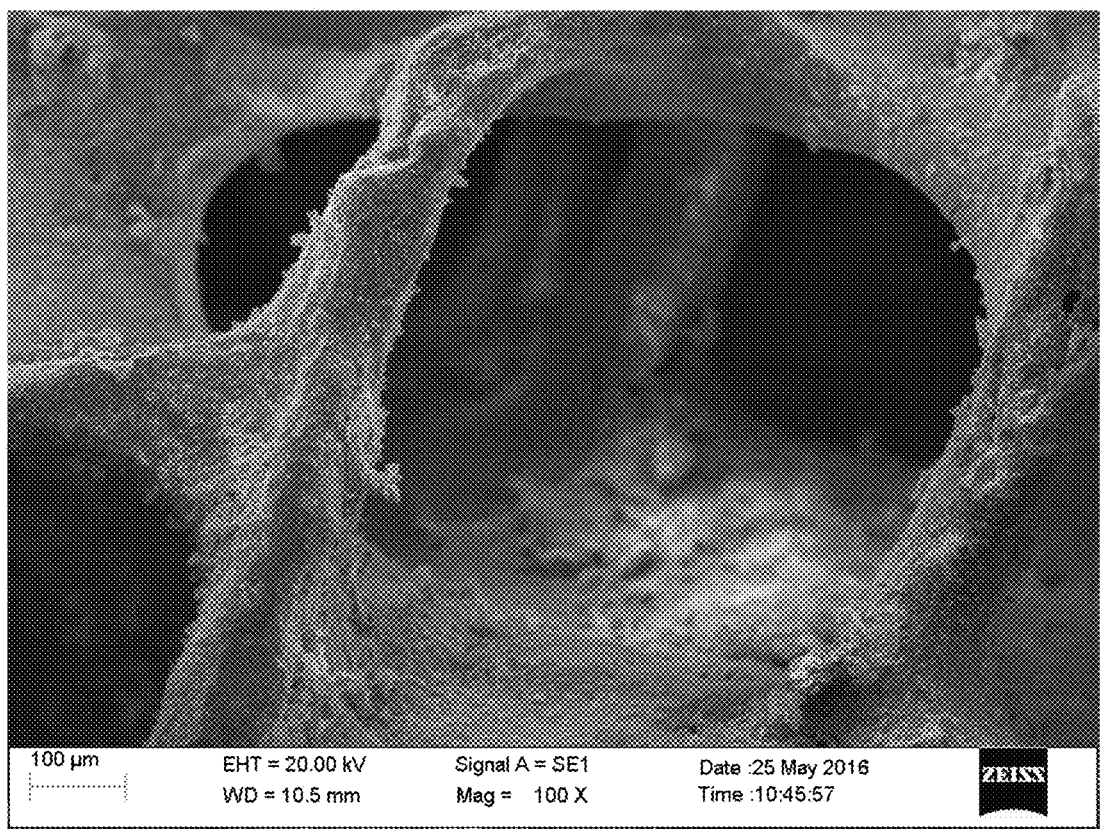
FIG. 3 is a scanning electron micrograph of a material of a product of the present invention after subjected to a dissolution and degradation test in simulated body fluid.

Medical sodium chloride injection is used as the simulated body fluid in the dissolution and degradation test in simulated body fluid. The solid-liquid ratio (mass to volume ratio) of the test material to the simulated body fluid is 1-2 g: 100 ml. The test material and the simulated body fluid were placed in a beaker having a cover, and the dissolution test in the simulated body fluid was performed under constant temperature condition of 37° C. The dissolution test duration was 4 weeks. Calcium ions, phosphorus ions and magnesium ions in the simulated body fluid were detected by AU5800 automatic biochemical analyzer. The mass of material at $4^{th}$ week was measured by a domestic electronic balance and the degradation rate was calculated. XRD analysis and SEM observation of the materials were performed before and at the end of the dissolution test. The test shows that the material has a good degradation rate (as shown in Tab. 2); in the early stage (within half a month) of the simulated body fluid test, most samples had higher concentrations of calcium ions in the simulated body fluids, which were maintained between 1-5 times of the median of normal reference values of human serum (as shown in FIG. 2); and active ionized magnesium were released. XRD analysis of the materials of the simulated body fluid test shows that the compositions and mass ratio of the material change over time, calcium sulfate and magnesium-containing calcium phosphate gradually decrease or disappear, and the scaffold material gradually changes to hydroxyapatite. The dissolution of materials and the redeposition of mineral components can be observed by scanning electron microscope (as shown in FIG. 3).

TABLE 2

Degradation rate of materials impregnated in simulated body fluids for 4 weeks

| Groups | degradation rate |
|---|---|
| hydroxyapatite | 1.56% |
| product A of the present invention | 33.11% |
| product B of the present invention | 21.6% |
| product C of the present invention | 43.2% |
| product D of the present invention | 38.23% |

3. Animal Bone Defect Repair Test

Figure 4:
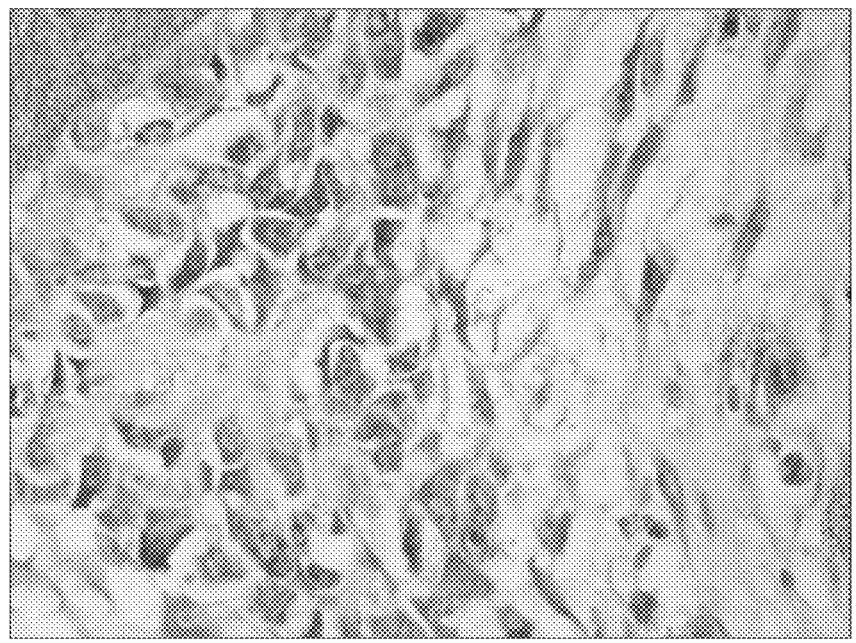
FIG. 4 is a histological diagram of a product of the present invention in an early stage of a transplant experiment.
Figure 5:
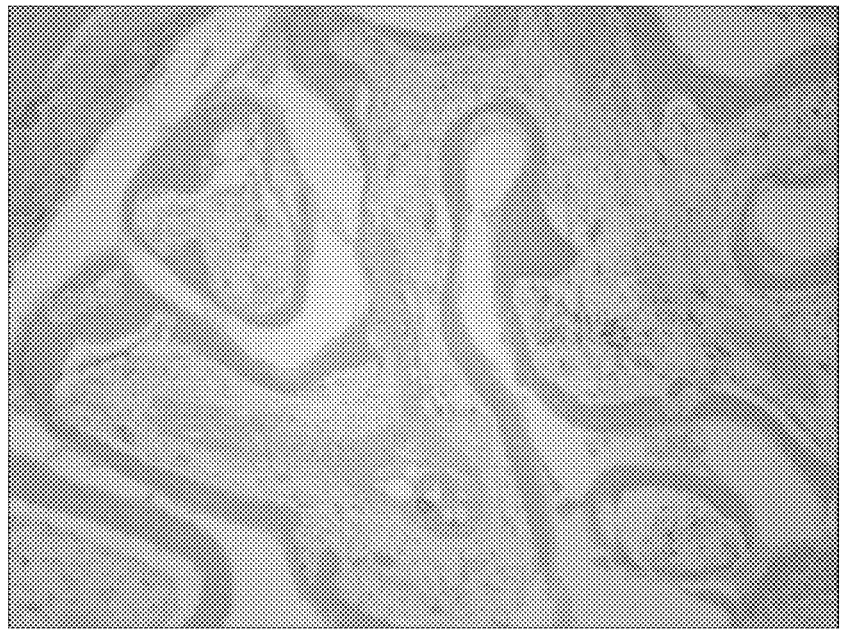
FIG. 5 is a histological diagram representation of a product of the present invention in an early stage of another transplant experiment.
Figure 6:
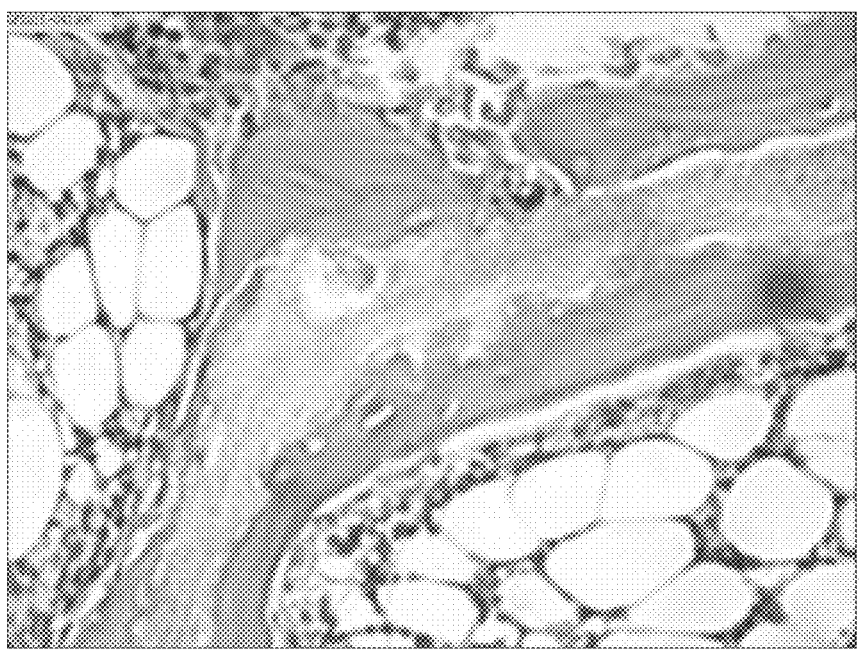
FIG. 6 is a histological diagram of a product of the present invention in a later stage of a transplant experiment.

In the early stage (1 week) of transplantation of the product of the present invention, cells and blood vessels can be seen to enter the whole space of the scaffold, and proliferation and differentiation of bone repair cells, and secretion of bone matrix by the bone repair cells can be seen (as shown in FIG. 4). Bone trabecula is formed within two weeks, and the new bone tissue is perfectly combined with the scaffold (as shown in FIG. 5). No immunological rejection or obvious inflammation was observed during the observation. The materials have good biocompatibility. During the observation, it was found that the new bone trabecula was gradually embedded in the wall of the scaffold material, indicating that the material could be gradually degraded (as shown in FIG. 6).

The above-mentioned embodiments are merely preferred embodiments of the present invention, which are not intended to limit the present invention in any form, and other variations and modifications of the present invention are possible without departing from the technical solutions as recited in the appended claims.

What is claimed is:

1. A method for preparing a degradable magnesium-containing calcium phosphate-calcium sulfate porous composite biological scaffold, comprising the following steps:
   (a) subjecting a calcined bovine cancellous bone mineral porous scaffold to a treatment using a magnesium source, a sulfur source and a phosphorus source;
   wherein the step (a) of subjecting the calcined bovine cancellous bone mineral porous scaffold to the treatment using the magnesium source, the sulfur source and the phosphorus source comprises the following step (a-1) or (a-2):
   (a-1) impregnating the calcined bovine cancellous bone mineral porous scaffold in a magnesium source solution to obtain a magnesium scaffold solution, then taking out a magnesium treated scaffold from the magnesium scaffold solution, and drying the magnesium treated scaffold, and subsequently putting the magnesium treated scaffold into a sulfur source and phosphorus source composite solution to obtain a composite scaffold solution, and performing a hydrothermal reaction on the composite scaffold solution to obtain a treated scaffold solution, or
   (a-2) subjecting the calcined bovine cancellous bone mineral porous scaffold to a hydrothermal reaction while impregnating the calcined bovine cancellous bone mineral porous scaffold in a magnesium source, sulfur source, and phosphorus source composite solution to obtain a treated scaffold solution;
   (b) taking out a treated scaffold from the treated scaffold solution and drying the treated scaffold; and
   (c) subjecting the treated scaffold to a high-temperature calcination to obtain the degradable magnesium-containing calcium phosphate-calcium sulfate porous composite biological scaffold,
   wherein, in the steps (a-1) and (a-2), the magnesium source comprises at least one magnesium compound selected from the group consisting of magnesium sulfate and magnesium hydrogen phosphate;
   in the steps (a-1) and (a-2), the sulfur source comprises sulfuric acid and soluble sulfate, and the soluble sulfate comprises at least one sulfate compound selected from the group consisting of sodium sulfate and magnesium sulfate; and
   in the steps (a-1) and (a-2), the phosphorus source comprises phosphoric acid and soluble phosphate, and the soluble phosphate comprises at least one phosphate compound selected from the group consisting of diammonium hydrogen phosphate, ammonium dihydrogen phosphate, magnesium hydrogen phosphate, a combination of magnesium hydrogen phosphate with diammonium hydrogen phosphate, and a combination of magnesium hydrogen phosphate with ammonium dihydrogen phosphate.

2. The method according to claim 1, wherein the hydrothermal reaction is carried out by a constant temperature hydrothermal method, the temperature is controlled at 70-90° C., and the reaction time is controlled for 8-36 h.

3. The method according to claim 1, wherein, the step (a) is the step (a-1) and in the step (a-1), a solid-liquid ratio of the calcined bovine cancellous bone mineral porous scaffold to the magnesium source solution is 10 g: 50-200 mL, and a solid-liquid ratio of the calcined bovine cancellous bone mineral porous scaffold to the sulfur source and phosphorus source composite solution is 10 g: 50-200 mL.

4. The method according to claim 1, wherein, the step (a) is the step (a-2) and in the step (a-2), a solid-liquid ratio of the calcined bovine cancellous bone mineral porous scaffold to the magnesium source, sulfur source, and phosphorus source composite solution is 10 g: 50-100 mL.

5. The method according to claim 1, wherein the high-temperature calcination is performed at a temperature of 750-900° C. and for a calcining time of 2-9 h.

6. The method according to claim 1, wherein a final concentration of magnesium ions in the magnesium source, the sulfur source and the phosphorus source is 0.05-0.2 mol/L.

7. The method according to claim 1, wherein in the magnesium source, the sulfur source and the phosphorus source, a final concentration of the sulfuric acid is 0.05-0.1 mol/L, and a final concentration of sulfate radicals provided by the soluble sulfate is 0.04-0.6 mol/L.

8. The method according to claim 1, wherein in the magnesium source, the sulfur source and the phosphorus source, a final concentration of the phosphoric acid is 0.85-1.7 wt %, and a final concentration of phosphorus provided by the soluble phosphate is 0.08-0.9 mol/L.

9. The method according to claim 1, wherein the degradable magnesium-containing calcium phosphate-calcium sulfate porous composite biological scaffold comprises a material composition selected from the group consisting of a combination of calcium sulfate and magnesium-containing calcium phosphate, a combination of calcium sulfate, magnesium-containing calcium phosphate and hydroxyapatite, a combination of calcium sulfate, magnesium-containing calcium phosphate, hydroxyapatite and calcium pyrophosphate, a combination of calcium sulfate, magnesium-containing calcium phosphate and calcium pyrophosphate, a combination of calcium sulfate and poly (magnesium-containing calcium hydrogen phosphate), and a combination of calcium sulfate, poly (magnesium-containing calcium hydrogen phosphate) and hydroxyapatite.

10. The method according to claim 1, wherein the calcined bovine cancellous bone mineral porous scaffold has a porosity of 70%-85% and an aperture of 400-1200 µm.

11. The method according to claim 1, wherein when the degradable magnesium-containing calcium phosphate-calcium sulfate porous composite biological scaffold is used, the degradable magnesium-containing calcium phosphate-calcium sulfate porous composite biological scaffold is degraded in a gradient fashion; and the degradable magnesium-containing calcium phosphate-calcium sulfate porous composite biological scaffold retains a three-dimensional interconnected mesh structure and a mechanical strength of the calcined bovine cancellous bone mineral porous scaffold, and at the same time, whiskers with a larger length-diameter ratio grow in a mesh, and a length-diameter ratio of the whiskers is 8-25:1, thereby effectively increasing the specific surface area of the degradable magnesium-containing calcium phosphate-calcium sulfate porous composite biological scaffold.

12. The method according to claim 1, wherein the calcined bovine cancellous bone mineral porous scaffold is made by a process comprising:
 (1) the bovine cancellous bone is cut into bone strips or bone blocks with a thickness of 0.5-1 cm to obtain raw bones;
 (2) the raw bones are placed in distilled water and cooked in a pressure cooker for 40-60 min, then washed with 40-60° C. drinking water, this step is repeated 4-6 times, then processed raw bones are obtained; and
 (3) the processed raw bones obtained in the step (2) is dried in a constant temperature drying oven at 80-120° C. for 12-24 h, then placed in a calciner to be calcined at 900-1200° C. for 8-12 h, and cooled to obtain the calcined bovine cancellous bone mineral porous scaffold.

13. A degradable magnesium-containing calcium phosphate-calcium sulfate porous composite biological scaffold, wherein the degradable magnesium-containing calcium phosphate-calcium sulfate porous composite biological scaffold is obtained by the method according to claim 1.

14. The degradable magnesium-containing calcium phosphate-calcium sulfate porous composite biological scaffold according to claim 13, wherein the calcined bovine cancellous bone mineral porous scaffold has a porosity of 70%-85% and an aperture of 400-1200 µm.

15. The degradable magnesium-containing calcium phosphate-calcium sulfate porous composite biological scaffold according to claim 13, comprising a material composition selected from the group consisting of a combination of calcium sulfate and magnesium-containing calcium phosphate, a combination of calcium sulfate, magnesium-containing calcium phosphate and hydroxyapatite, a combination of calcium sulfate, magnesium-containing calcium phosphate, hydroxyapatite and calcium pyrophosphate, a combination of calcium sulfate, magnesium-containing calcium phosphate and calcium pyrophosphate, a combination of calcium sulfate and poly (magnesium-containing calcium hydrogen phosphate), and a combination of calcium sulfate, poly (magnesium-containing calcium hydrogen phosphate) and hydroxyapatite.

16. The degradable magnesium-containing calcium phosphate-calcium sulfate porous composite biological scaffold according to claim 13, wherein when the degradable magnesium-containing calcium phosphate-calcium sulfate porous composite biological scaffold is used, the degradable magnesium-containing calcium phosphate-calcium sulfate porous composite biological scaffold is degraded in a gradient fashion; and the degradable magnesium-containing calcium phosphate-calcium sulfate porous composite biological scaffold retains a three-dimensional interconnected mesh structure and a mechanical strength of the calcined bovine cancellous bone mineral porous scaffold, and at the same time, whiskers with a larger length-diameter ratio grow in a mesh, and a length-diameter ratio of the whiskers is 8-25:1, thereby effectively increasing the specific surface area of the degradable magnesium-containing calcium phosphate-calcium sulfate porous composite biological scaffold.

\* \* \* \* \*